(12) United States Patent
Kobayashi (10) Patent No.: US 8,734,335 B2
(45) Date of Patent: May 27, 2014

(54) ELECTRONIC ENDOSCOPE

(75) Inventor: Shotaro Kobayashi, Saitama (JP)

(73) Assignee: Hoya Corporation, Tokyo (JP)

( * ) Notice: Subject to any disclaimer, the term of this patent is extended or adjusted under 35 U.S.C. 154(b) by 1925 days.

(21) Appl. No.: 11/551,534

(22) Filed: Oct. 20, 2006

(65) Prior Publication Data
US 2007/0093691 A1    Apr. 26, 2007

(30) Foreign Application Priority Data
Oct. 21, 2005    (JP) ................ P2005-307121

(51) Int. Cl.
*A61B 1/06*    (2006.01)

(52) U.S. Cl.
USPC ............. 600/178; 600/180; 600/181

(58) Field of Classification Search
CPC .. A61B 1/0638; A61B 1/0646; A61B 1/0661; A61B 1/0669
USPC ........... 600/109, 118, 160, 178, 180, 181, 600/476–478; 362/572, 574
See application file for complete search history.

(56) References Cited

U.S. PATENT DOCUMENTS

| | | | | |
|---|---|---|---|---|
| 4,773,097 A * | 9/1988 | Suzaki et al. | ................. | 382/128 |
| 4,821,117 A * | 4/1989 | Sekiguchi | ....................... | 348/68 |
| 5,001,556 A * | 3/1991 | Nakamura et al. | ............. | 348/70 |
| 5,187,572 A * | 2/1993 | Nakamura et al. | ............. | 348/68 |
| 6,280,378 B1 * | 8/2001 | Kazuhiro et al. | ............. | 600/160 |
| 6,473,637 B1 * | 10/2002 | Hayashi | ........................ | 600/477 |
| 6,498,948 B1 | 12/2002 | Ozawa et al. | | |
| 6,527,708 B1 | 3/2003 | Nakamura et al. | | |
| 6,602,186 B1 * | 8/2003 | Sugimoto et al. | ............. | 600/126 |

(Continued)

FOREIGN PATENT DOCUMENTS

| | | |
|---|---|---|
| JP | 7-155292 | 6/1995 |
| JP | 10-151104 | 6/1998 |

(Continued)

OTHER PUBLICATIONS

English language Abstract of JP 2003-033324.

(Continued)

*Primary Examiner* — Anhtuan T Nguyen
*Assistant Examiner* — William Chou
(74) *Attorney, Agent, or Firm* — Greenblum & Bernstein, P.L.C.

(57) ABSTRACT

An electronic endoscope includes a white light source, an excitation light source, an imaging device, and a light amount controller. The white light source emits white light for illuminating a subject. The excitation light source emits excitation light for generating fluorescent light on the subject. The imaging device generates first image signals by receiving reflected light of the white light, and generates second image signals by receiving the fluorescent light. The light amount controller controls the amount of the white light to lower the difference between a reflected light luminance and a fluorescent light luminance, so that a normal image corresponding to the first image signals and a fluorescent image corresponding to the second image signals that are both real-time images representing the same subject at the time of receiving the reflected light and the fluorescent light can be generated.

13 Claims, 9 Drawing Sheets

(56) References Cited

U.S. PATENT DOCUMENTS

| | | | |
|---|---|---|---|
| 6,635,011 B1* | 10/2003 | Ozawa et al. | 600/178 |
| 7,667,180 B2* | 2/2010 | Maeda | 250/208.1 |
| 7,675,017 B2* | 3/2010 | Yamaguchi | 250/208.1 |
| 2003/0035301 A1* | 2/2003 | Gardiner et al. | 362/583 |
| 2003/0176768 A1* | 9/2003 | Gono et al. | 600/109 |
| 2004/0046865 A1* | 3/2004 | Ueno et al. | 348/70 |
| 2004/0186351 A1* | 9/2004 | Imaizumi et al. | 600/160 |
| 2005/0288556 A1* | 12/2005 | Sugimoto | 600/160 |
| 2006/0178565 A1* | 8/2006 | Matsui et al. | 600/160 |
| 2008/0009669 A1* | 1/2008 | Ozawa et al. | 600/101 |
| 2008/0249368 A1* | 10/2008 | Takei | 600/178 |

FOREIGN PATENT DOCUMENTS

| | | |
|---|---|---|
| JP | 2003-033324 | 2/2003 |
| JP | 2005-087450 | 4/2005 |
| JP | 2005-137755 | 6/2005 |

OTHER PUBLICATIONS

English language Abstract of JP 2005-137755.

Japan Office action, dated Feb. 1, 2011 along with an english translation thereof.

* cited by examiner

(a) WL TABLE

| LIGHT AMOUNT LEVEL | APERTURE DRIVE VOLTAGE |
|---|---|
| LEVEL+2 | 10V |
| LEVEL+1 | 8V |
| LEVEL 0 | 6V |
| LEVEL−1 | 4V |
| LEVEL−2 | 2V |

(b) TWIN TABLE

| LIGHT AMOUNT LEVEL | APERTURE DRIVE VOLTAGE |
|---|---|
| LEVEL+2 | 9V |
| LEVEL+1 | 7V |
| LEVEL 0 | 5V |
| LEVEL−1 | 3V |
| LEVEL−2 | 1V |

(c) MIX TABLE

| LIGHT AMOUNT LEVEL | APERTURE DRIVE VOLTAGE |
|---|---|
| LEVEL+2 | 8V |
| LEVEL+1 | 6V |
| LEVEL 0 | 4V |
| LEVEL−1 | 2V |
| LEVEL−2 | 0V |

FIG. 9

ELECTRONIC ENDOSCOPE

BACKGROUND OF THE INVENTION

1. Field of the Invention

The present invention relates to an electronic endoscope, especially to an electronic endoscope that can display a fluorescent image.

2. Description of the Related Art

Currently, an electronic endoscope that enables a so-called fluorescence observation is known. In such an electronic endoscope, the property is utilized that when excitation light is emitted, a normal part of an observation subject generates fluorescent light; on the other hand, a diseased part, such as a cancer part, generates no fluorescent light. In certain such electronic endoscopes, a plurality of imaging optical systems are provided, so that a fluorescent image and a normal image based on reflected light of white light are generated and displayed on a monitor simultaneously.

On the other hand, in a current electronic endoscope that enables a fluorescence observation and that has a single imaging optical system, obtained normal images and fluorescent images are once stored, then processes are carried out on each of them. After carrying out the processes, a normal image and a fluorescent image are displayed on a monitor. The reason for carrying out different processes for a normal image and for a fluorescent image is that the fluorescent light from a body organ based on the excitation light is weaker than the reflected light of the white light, so that image signals based on the fluorescent light should be amplified; on the other hand, amplifying image signals based on the reflected light of the white light may cause halation in a normal image, so a subject may not be observed.

Providing a plurality of imaging optical systems in an electronic endoscope complicates the device, increases the manufacturing cost. On the other hand, in a current electronic endoscope having a single imaging optical system, a normal image and a fluorescent image as real time images of the same subject can not be generated by brightness control, and can not be displayed.

SUMMARY OF THE INVENTION

Therefore, an objective of the present invention is to provide an electronic endoscope that can generate and display a normal image and a high-quality fluorescent image of the same subject as the normal image, as real time images by brightness control of a single imaging optical system.

An electronic endoscope according to the present invention includes a white light source, an excitation light source, an imaging device, and a light amount controller. The white light source emits white light for illuminating a subject. The excitation light source emits excitation light for generating fluorescent light on the subject. The imaging device generates first image signals by receiving reflected light of the white light, the reflected light being reflected on the subject, and generates second image signals by receiving the fluorescent light. The light amount controller controls the amount of the white light. The light amount controller controlling the amount of the white light to lower the difference between a reflected light luminance (luminance of the reflected light received by the imaging device) and a fluorescent light luminance (luminance of the fluorescent light received by the imaging device), so that a normal image and a fluorescent image that are both real-time images representing the same subject at the time of receiving the reflected light and the fluorescent light can be generated. The normal image corresponds to the first image signals, and the fluorescent image corresponds to the second image signals.

The light amount controller may control the amount of the white light to lower the difference between a first luminance component that is the luminance component of the first image signals and a second luminance component that is the luminance component of the second image signals. The light amount controller may include an aperture and an aperture position controller that controls the position of the aperture. The electronic endoscope may further include a data memory in which aperture control data for controlling the position of the aperture is stored, and a data reader that reads the aperture control data, the aperture position controller may control the position of the aperture based on the aperture control data read by the data reader and the reflected light luminance. In the data memory, a plurality of the aperture control data may be stored, and the data reader may read the aperture control data in accordance with a command of a user.

The aperture control data, to lower the amount of the white light and to render the reflected light luminance and the fluorescent light luminance almost identical to each other, may be stored in the data memory, and the light amount controller may lower the amount of the white light based on the aperture control data, so that a pseudo-color image corresponding to the first image signals and the second image signals can be generated.

The electronic endoscope may further include a luminance component memory in which first luminance component data representing the luminance component of the first image signals is written; the aperture position controller may control the position of the aperture based on the first luminance component data written to the luminance component memory, not based on second luminance component data representing the luminance component of the second image signals.

The electronic endoscope may further include an image display that displays the normal image and the fluorescent image simultaneously.

The electronic endoscope may further include a light controller that controls the emission of the white light and the excitation light so that the white light and the excitation light are emitted alternately, each for a predetermined time.

BRIEF DESCRIPTION OF THE DRAWINGS

The present invention will be better understood from the description of the preferred embodiments of the invention set forth below together with the accompanying drawings, in which.

DESCRIPTION OF THE PREFERRED EMBODIMENTS

Hereinafter, the preferred embodiments of the present invention are described with reference to the attached drawings.

Figure 1:
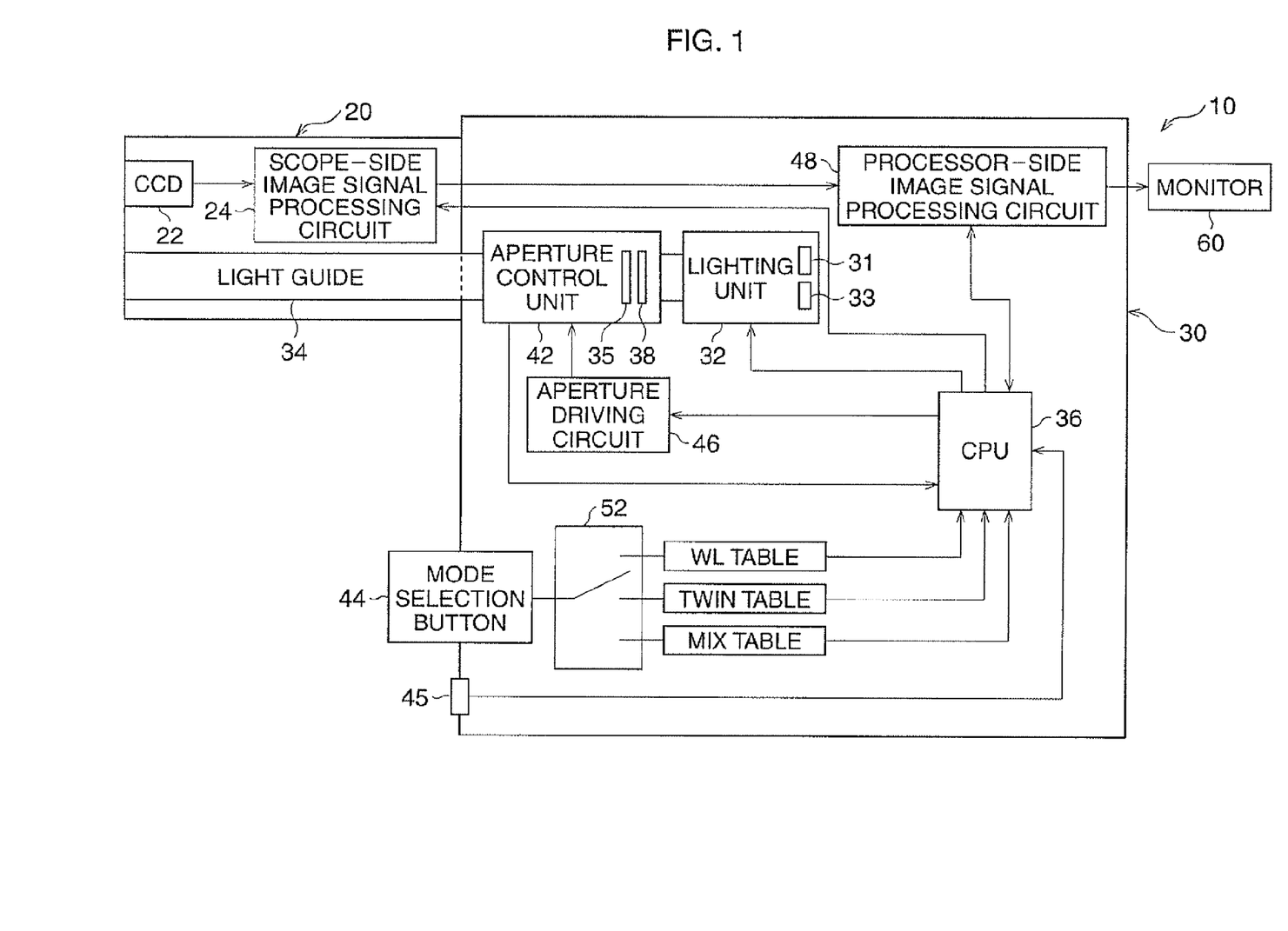
FIG. 1 is a block diagram of an electronic endoscope of the first embodiment.

As shown in FIG. 1, an electronic endoscope 10 includes a scope 20 and a processor 30. The scope 20 is used for observing and photographing inside a body cavity. The processor 30 provides illuminating light for illuminating a subject to the scope 20, and processes image signals transferred from the scope 20. Further, in the electronic endoscope 10, a monitor 60 that is connected to the processor 30 and that is used for displaying a subject image is included.

In the processor 30, a lighting unit 32 and a CPU 36 for controlling the entirety of the processor 30 are provided. A white light source 31 to emit white light that is one of the illuminating lights for illuminating a subject, and an excitation light source 33 to emit excitation light that is one of the illuminating lights for generating fluorescent light on a subject, are provided in the lighting unit 32.

The white light and the excitation light emitted by the lighting unit 32 are collected by a collective lens (not shown), their amounts are adjusted by an aperture 38 in an aperture control unit 42 that is driven by an aperture driving circuit 46, and then the lights enter a light guide 34. The white light or excitation light enters the light guide 34, passes through the light guide 34, and is emitted to a subject from the end of the scope 20. Note that in the aperture control unit 42, a rotary shutter 35 and other components are provided, so that emission of the illuminating lights is controlled. That is, the white light and the excitation light are emitted to a subject alternately, each for a predetermined time, such as for one field.

The reflected light of the white light reflected on a subject, or the fluorescent light generated by the excitation light, passes through an objective lens (not shown), and enters a CCD 22. Then, image signals based on the reflected light of the white light (first image signals) and image signals based on the fluorescent light (second image signals) are generated. The generated image signals are read for each one field, that is for each one-sixtieth second successively, then are transmitted to a scope-side image signal processing circuit 24, via a CDS circuit and other components (not shown).

In the scope-side image signal processing circuit 24, the read image signals are amplified and converted from analog image signals to digital image signals. Further, various processes such as white balance adjustment are carried out on the digital image signals, then luminance signals and color-difference signals are generated. The luminance signals and color-difference signals are transmitted to a processor-side image signal processing circuit 48, converted to NTSC signals, and then the NTSC signals are output to the monitor 60. As a result, a subject image is displayed on the monitor 60.

Note that in the scope-side image signal processing circuit 24, the gain for amplifying the image signals is adjusted under the control of the CPU 36. That is, the signal level of the image signals based on the fluorescent light (hereinafter called fluorescent image signals) is significantly smaller than that of the image signals based on the reflected light of the white light (hereinafter called normal image signals). Therefore, in the amplification process for the fluorescent image signals, greater gain is set than that in the amplification process for the normal image signals.

The luminance signals generated in the scope-side image signal processing circuit 24 are further transferred to the CPU 36 from the processor-side image signal processing circuit 48. The CPU 36 controls the aperture control unit 42 via the aperture driving circuit 46, then the CPU 36 adjusts the position of the aperture 38. From the aperture control unit 42, data representing the actual position of the aperture 38 are transmitted to the CPU 36, so that the CPU 36 can adjust the position of the aperture 38 accurately, based on this feedback.

On the surface on the processor 30, a mode selection button 44 is provided. In the electronic endoscope 10, a plurality of image modes can be selected and set by depression of the mode selection button 44. That is, a normal image mode where a normal image is generated based on the reflected light of the white light and displayed on the monitor 60; a fluorescent image mode where a fluorescent image based on the fluorescent light is generated and displayed; a plurality images mode where a normal image and a fluorescent image are simultaneously generated and displayed; and a pseudo-color image mode where a pseudo-color image based on the reflected light of the white light and the fluorescent light (i.e., corresponding to the normal image signals and the fluorescent image signals) is generated and displayed can be selected.

When the signals representing that the mode selection button 44 is depressed are transmitted to the CPU 36, a mode in accordance with a command of a user is set by the CPU 36. If the fluorescent image mode is selected, the CPU 36 controls the lighting unit 32 and the aperture driving circuit 46 so that only the excitation light from the excitation light source 33 enters the light guide 34.

In the processor 30, a table memory (a data memory) 52 is provided. In the table memory 52, dimmer tables, which are data to adjust the position of the aperture 38 for rendering the amount of the white light entering the light guide 34 suitable, are stored. In the dimmer tables, a WL table for the normal image mode, a TWIN table for the plurality images mode and a MIX table for the pseudo-color image, are included. Note that a dimmer table for the fluorescent image mode is not provided, because adjustment of the amount of the white light is not required in the fluorescent image mode.

When the normal image mode is set by depression of the mode selection button 44, the CPU 36 controls the lighting unit 32 and other components so that only the white light from the white light source 31 enters the light guide 34, and reads the WL table from the table memory 52. Then, the CPU 36 controls the position of the aperture 38 via the aperture driving circuit 46, based on the WL table and the luminance signals of the reflected light of the white light from the processor-side image signal processing circuit 48.

When the plurality images mode or the pseudo-color image mode is set, the CPU 36 controls the lighting unit 32, the rotary shutter 35, and other components so that the white light and the excitation light enter the light guide 34 alternately, each for one field, and the CPU 36 reads the TWIN table or the MIX table from the table memory 52. Then, the CPU 36 controls the position of the aperture 38 via the aperture driving circuit 46, based on the read table and the luminance signals from the processor-side image signal processing circuit 48. Note that the CPU 36 carries out emission control for each one field, based on the field signals transmitted from the scope 20.

A light amount control button 45 is provided close to the mode selection button 44. The amount of the white light entering the light guide 34 can be adjusted step by step by depression of the light amount control button 45, regardless of whether the normal image mode, the plurality images mode, or the pseudo-color image mode is set.

Figure 2:
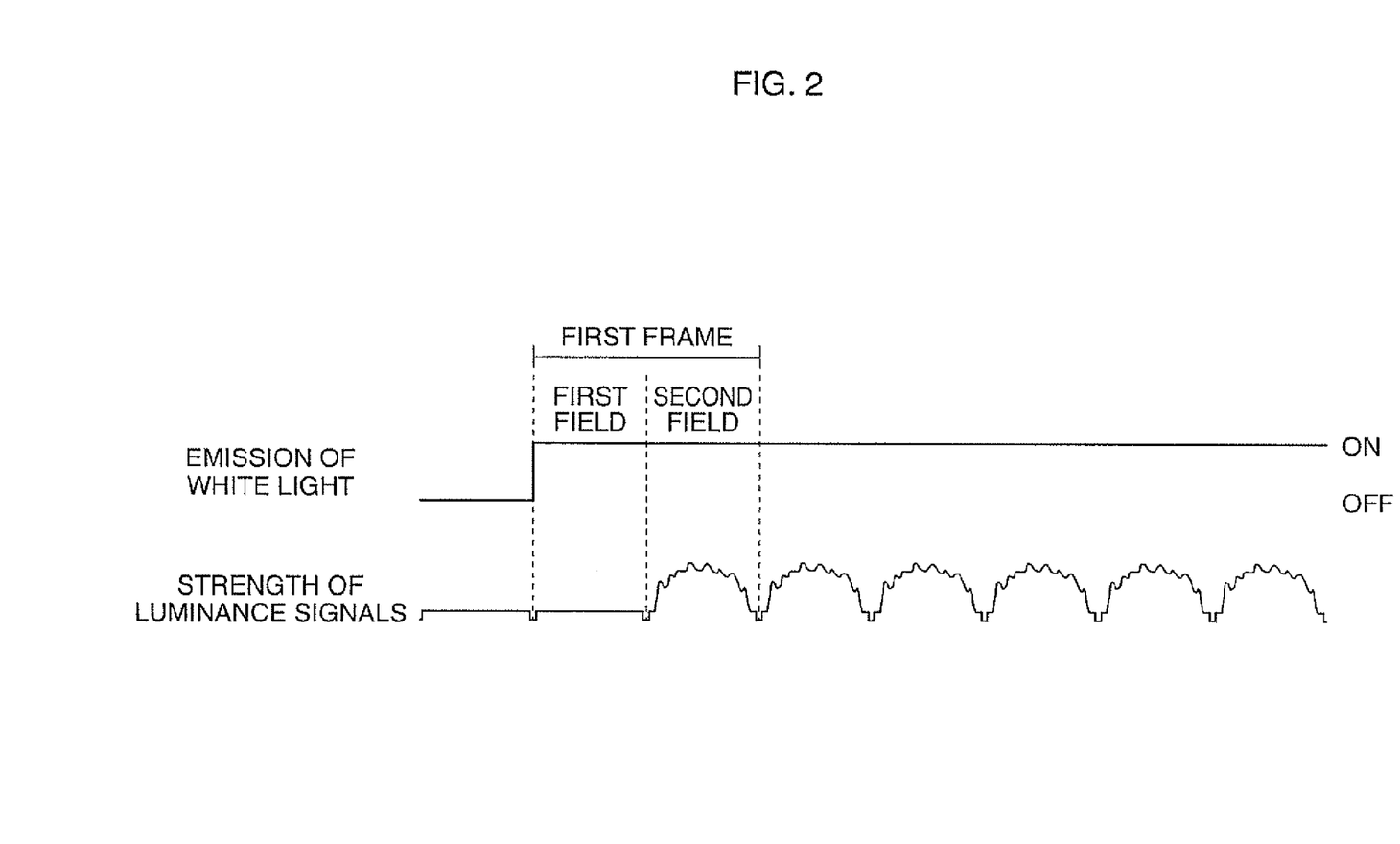
FIG. 2 is a timing chart representing the changes in the emission of the white light and in the strength of the luminance signals over time in a normal image mode of the first embodiment.

When the normal image mode is set, the white light is emitted to a subject from the lighting unit 32 via the light guide 34, then the luminance signals are generated based on the reflected light thereof. As shown in FIG. 2, the strength of the generated luminance signals (that is, the luminance component of the normal image signals) is approximately constant without a large gap, so long as a sudden change on a subject does not occur.

The CPU 36 takes the average of the strength of the luminance signals for a predetermined time of a plurality of frames, and causes the aperture driving circuit 46 to control the aperture 38 to be in the suitable position. The reason is that adjusting the position of the aperture 38 in a short period, such as one field, is impossible.

Figure 3:
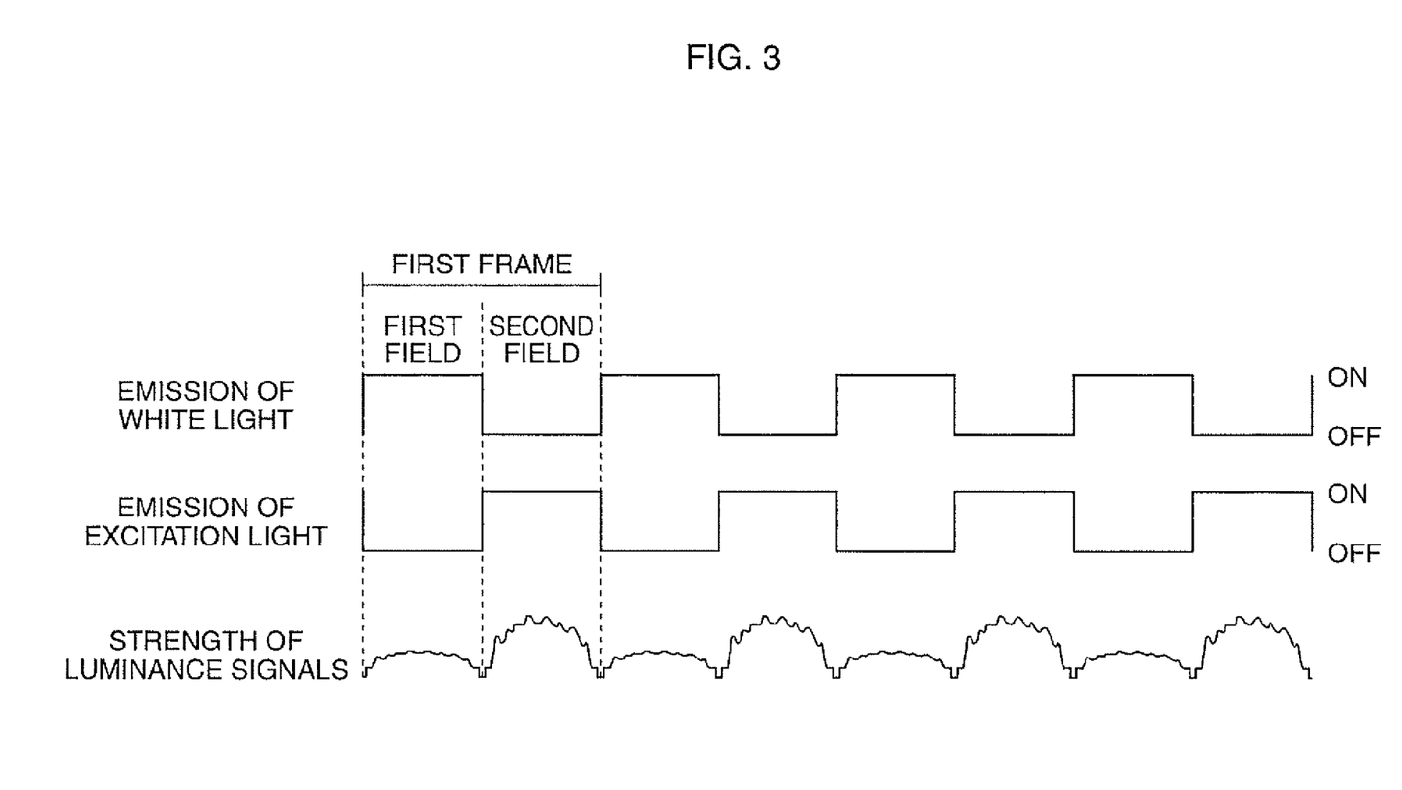
FIG. 3 is a timing chart representing changes in the emission of the white light and in the strength of the luminance signals over time in a plurality images mode and a pseudo-color image mode of the first embodiment.

On the other hand, when the plurality images mode or the pseudo-color image mode is set, the white light and the excitation light are emitted alternately in the first field and the second field of one frame of one-thirtieth of a second (see FIG. 3). The strength of the luminance signals that are generated based on the reflected light of the white light emitted in the first field, and that are read in the second field, is much higher than the strength of the luminance signals that are generated based on the excitation light emitted in the second field (that is, the luminance component of the fluorescent image signals).

In the plurality images mode or the pseudo-color image mode, the CPU 36 causes the aperture driving circuit 46 to adjust the position of the aperture 38, based on the average strength of the luminance signals for a predetermined time of more than a plurality of frames, similarly to in the normal image mode.

As it is clear from the above, in the plurality images mode or the pseudo-color image mode where the excitation light and the white light are emitted at almost the same time, the above-explained average strength of the luminance signals is much lower than the strength of the luminance signals of the reflected light of the white light. Therefore, if the position of the aperture 38 is adjusted based on only the average strength of the luminance signals in the plurality images mode or in the pseudo-color image mode, the aperture driving circuit 46 causes the aperture 38 to move to a position where the amount of the white light entering the light guide 34 is largely excessive, under the control of the CPU 36.

As a result, in the plurality images mode, in a normal image displayed on the monitor 60 simultaneously with a fluorescent image, halation may occur, and a subject in the normal image may become invisible. In the pseudo-color image mode where a pseudo-color image is generated by combining the normal image signals and the fluorescent image signals that are read in the continuous fields, a low-quality pseudo-color image may be generated by combining image signals having largely different luminance levels.

Figure 4:
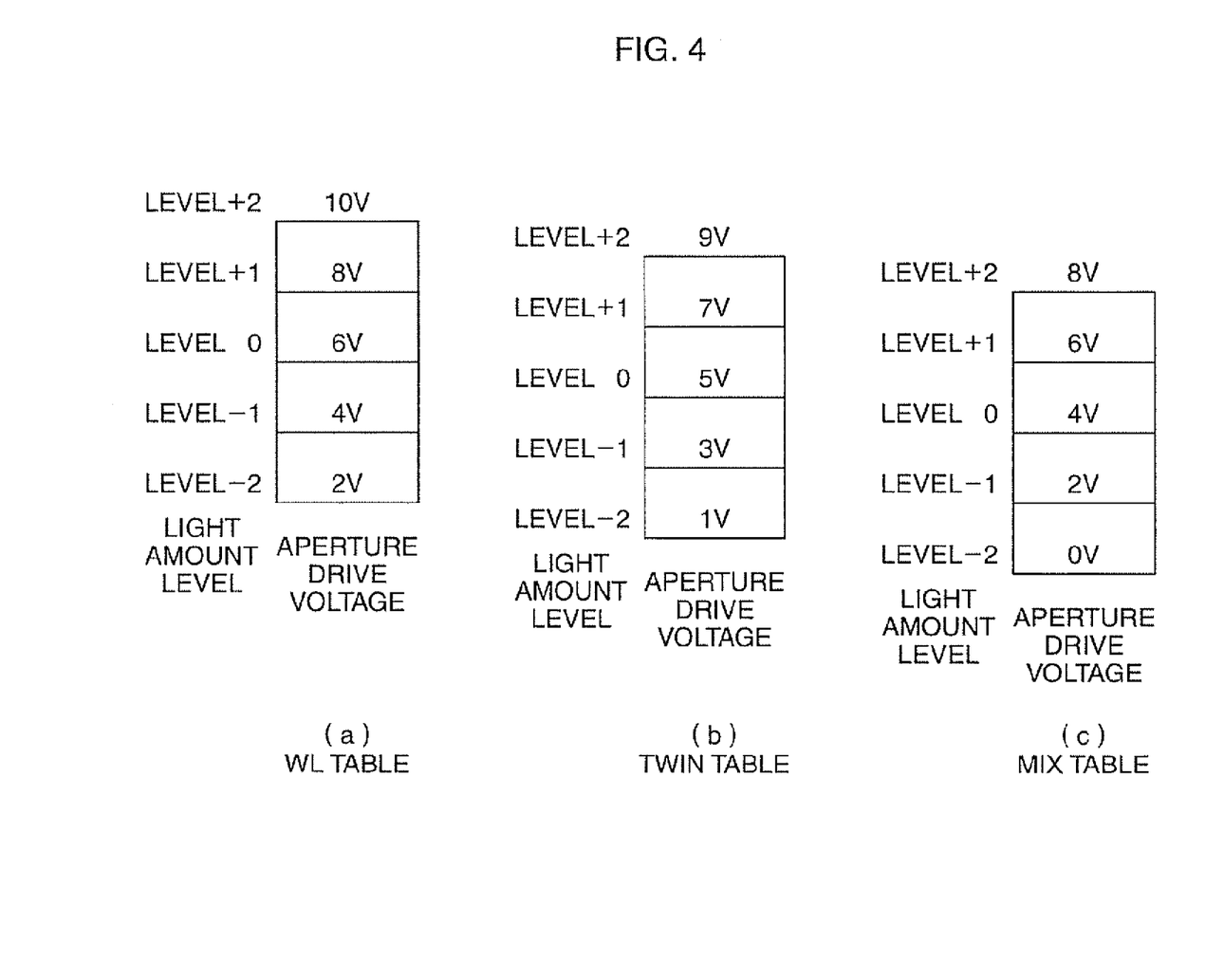
FIG. 4 is a view representing an example of a dimmer table.

To adjust the amount of the white light to prevent a low-quality image due to halation or other reasons, the dimmer tables explained above are used (see FIG. 4). FIG. 4(a) represents the WL table for the normal image mode, FIG. 4(b) represents the TWIN table for the plurality images mode, and FIG. 4(c) represents the MIX table for the pseudo-color image mode.

The dimmer tables are correspondence tables representing relations between the light amount level of the white light which is set step by step, by depression of the light amount control button 45, and aperture drive voltages provided to the aperture driving circuit 46 to move the aperture 38 to the position where the white light of each light amount level is emitted to a subject. Based on these dimmer tables, the position of the aperture 38 is adjusted in accordance with the set light amount level. When a different light amount level is set, the aperture 3B is moved to the position corresponding to the newly set light amount level. When the aperture drive voltage is higher, the aperture 38 moves to a position where a lower amount of the white light passes through the aperture 38 and enters a light guide 34.

FIGS. 4(a) to (c) represent that the amount level of the white light is lower in the order of the normal image mode, the plurality images mode, and the pseudo-color image mode, when the same light amount level is set. The reason for a lower amount of white light in the pseudo-color image mode than that in the plurality images mode is as follows. In the plurality images mode, lowering the level of the luminance component of the normal image signals to be closer to that of the fluorescent image signals is required to prevent halation in a normal image; on the other hand, in the pseudo-color image mode, lowering the level of the luminance component of the normal image signals to be almost identical to that of the fluorescent image signals is required to improve the quality of a pseudo-color image to be generated.

Note that the level "0" in the dimmer tables represents a default value of the light amount levels, and that when the light amount control button 45 is depressed, levels "+1", "+2", or "−1", "−2" are set. The position of the aperture 38 is adjusted not only by the dimmer tables, but also by the luminance signals, as explained above.

The brightness control routine (see FIG. 5) starts when the electronic endoscope 10 starts. At step S10, it is determined whether setting or changing an image mode by the depression of the mode selection button 44 is commanded or not. When it is determined that setting or changing an image mode has been commanded, the process proceeds to step S11. At step S11, it is determined whether setting or changing to the normal image mode has been commanded or not, when it is determined that setting or changing to the normal image mode has been commanded, the process proceeds to step S12, and when it is determined that the normal image mode has not been commanded, the process proceeds to step S13.

Figure 5:
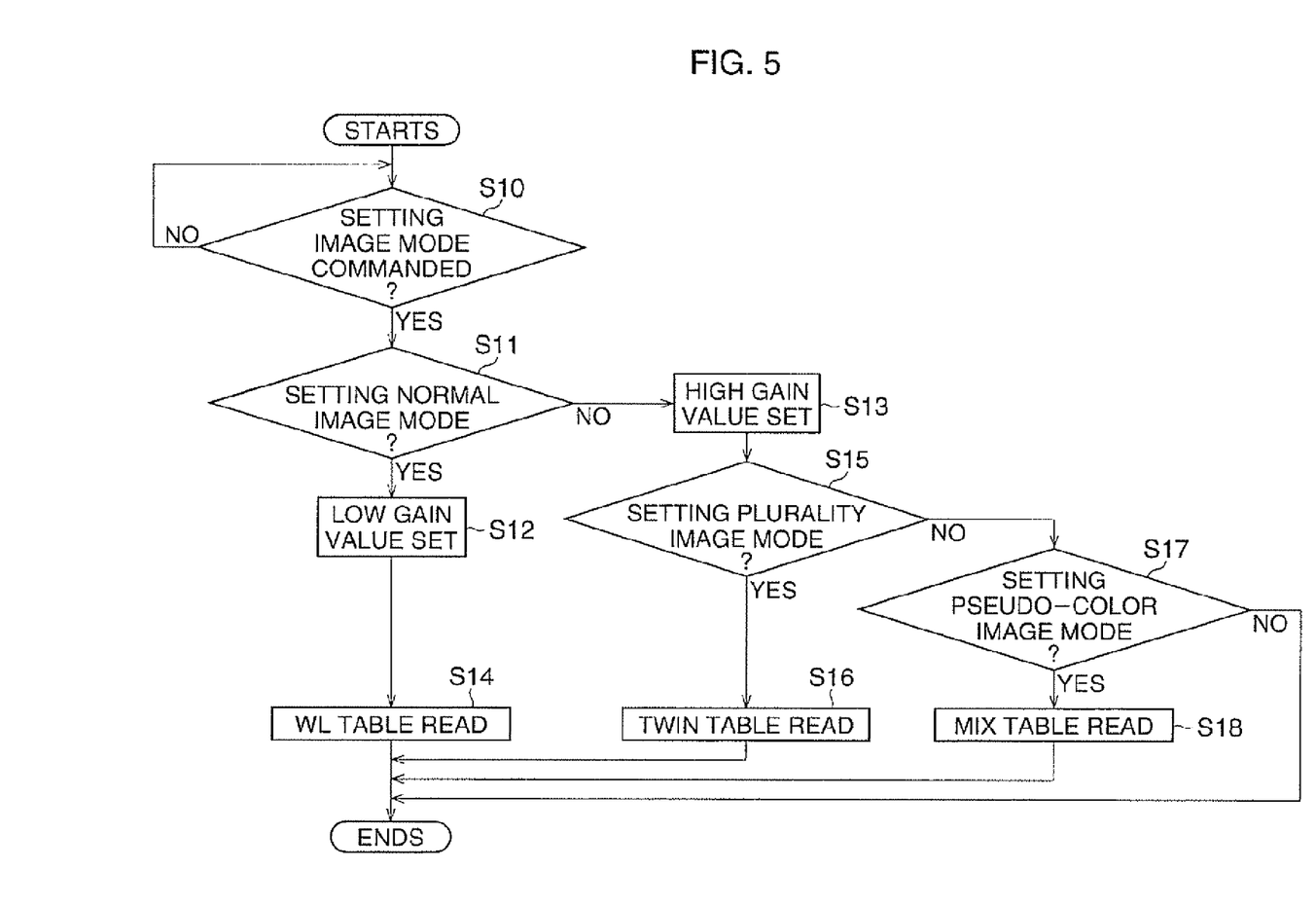
FIG. 5 is a flowchart of a brightness control routine in the electronic endoscope.

At step S12, the gain for an amplifying process in the scope-side image signal processing circuit 24 is set to be a low gain value for processing the normal image signals, then, the process proceeds to step S14. At step S14, the WL table is read from the table memory 52, and the brightness control routine ends.

At step S13, since the gain for an amplifying process is set to be a high gain value, because the high gain value is suitable for processing the fluorescent image signals, the process proceeds to step S15. At step S15, it is determined whether setting the plurality images mode has been commanded or not. When it is determined that the plurality images mode has been commanded, the process proceeds to step S16, and when it is determined that the plurality images mode has not been commanded, the process proceeds to step S17. At step S16, the TWIN table is read from the table memory 52, and then the brightness control routine ends.

At step S17, it is determined whether setting the pseudo-color image mode has been commanded or not. When it is determined that setting the pseudo-color image mode has been commanded, the process proceeds to step S18. At step S18, the MIX table is read from the table memory 52, and then the brightness control routine ends.

On the other hand, when it is determined that setting the pseudo-color image mode has not been commanded at step S17, this means that the image mode that is commanded to be set at step S10 is the fluorescent image mode where a dimmer table is not necessary, therefore, the brightness control routine ends without reading a dimmer table.

As explained above, in the electronic endoscope 10 of the first embodiment, a normal image and a fluorescent image representing the same subject as the normal image which have high qualities are generated. Further, the normal image and the fluorescent image can be generated and displayed as real time images, because storing image signals for generating the normal image and the fluorescent image in a memory, and carrying out different processes to the image signals for these images, are not required.

In the electronic endoscope 10 of the first embodiment, only a single imaging optical system, including the CCD 22 and other components, is provided, so that the structure of the electronic endoscope 10 can be simplified.

Note that the dimmer tables represented in FIG. 4 are only examples, and that dimmer tables actually used may not be limited to those represented in FIG. 4. For example, aperture drive voltages in accordance with the light amount levels may be set geometrically, as opposed to arithmetically as in the examples.

Hereinafter, a second embodiment of the present invention is explained, mainly focusing on the differences from the first embodiment. Note that in FIG. 6, the same components as those in the first embodiment have the same reference numerals, except for the electronic endoscope 50.

Figure 6:
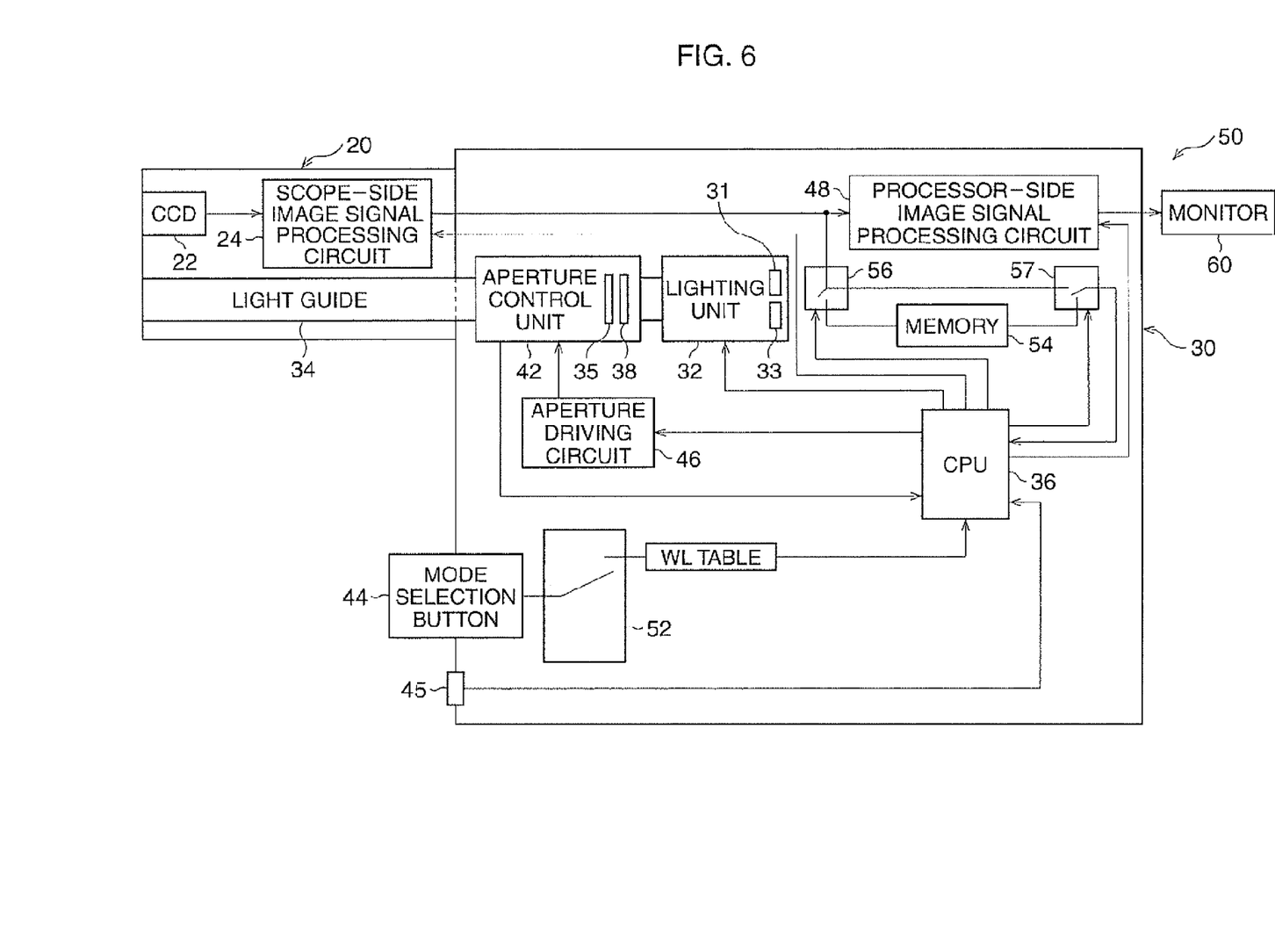
FIG. 6 is a block diagram of an electronic endoscope of the second embodiment.

In the processor 30 of the electronic endoscope 50 of the second embodiment, a luminance component memory 54 is provided (see FIG. 6). Further, a first transfer switch 56 and a second transfer switch 57 are provided on the input side of the luminance component memory 54 and the output side thereof, respectively. The luminance component memory 54 and the first and second transfer switches 56 and 57 are provided for preventing deterioration of the quality of a normal image that is generated and displayed in the plurality images mode by a different method from one in the first embodiment.

Figure 7:
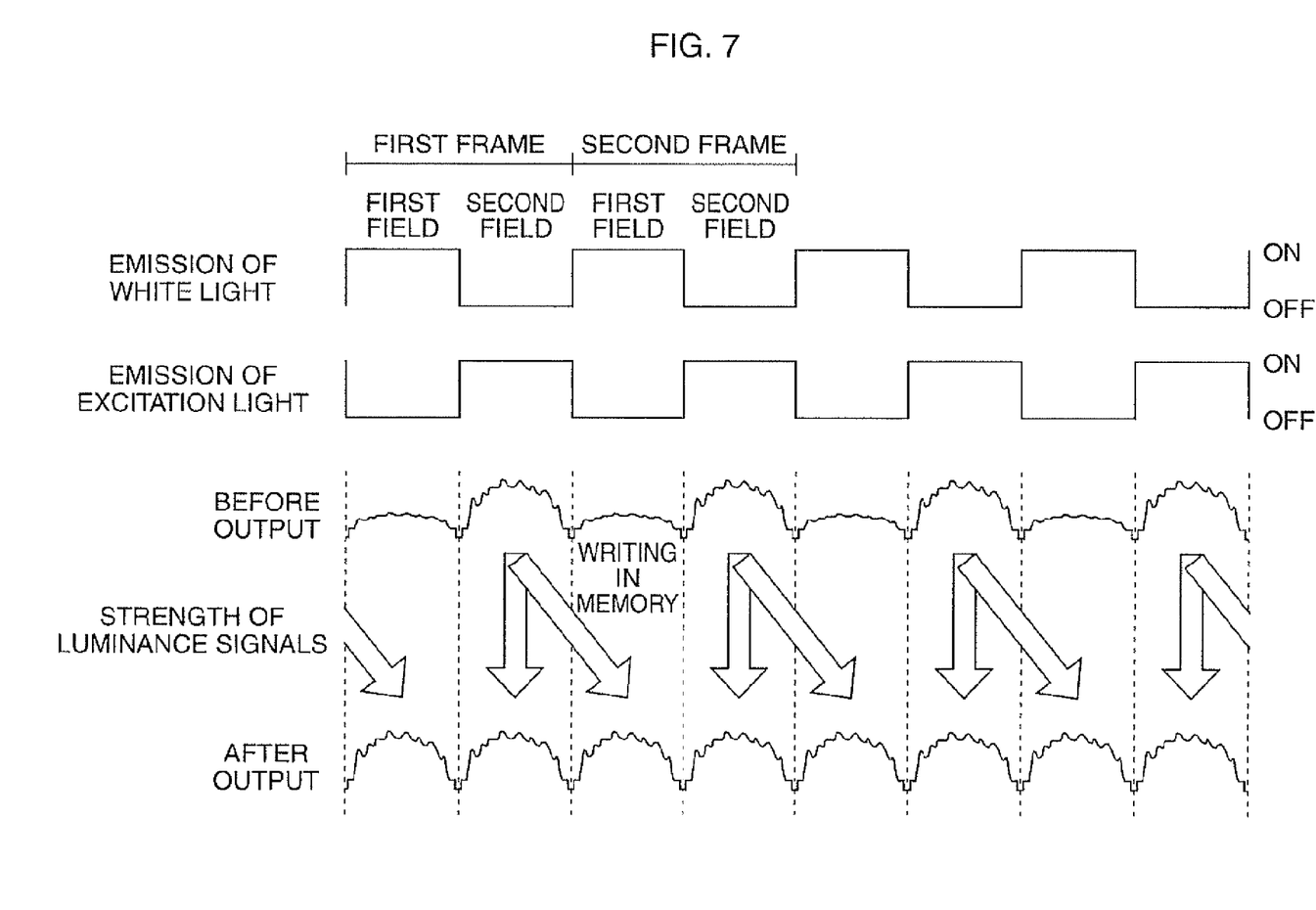
FIG. 7 is a timing chart representing change in the strength of the luminance signals over time in a plurality images mode of the second embodiment.

In the second embodiment, in the plurality images mode, where the white light and the excitation light are emitted alternately in the first field and the second field of one frame, only the luminance component of the normal image signals is transmitted to the CPU 36, as represented in FIG. 7. This control of the transmission of the image signals causes the CPU 36 to determine that the average strength of the luminance signals for a predetermined time of a plurality of frames has not been lowered.

That is, the luminance component of the fluorescent image signals is not written to the luminance component memory 54, and the luminance component of the normal image signals based on the reflected light of the white light, which is received by the CCD 22 one field before the fluorescent light is received, is written to the luminance component memory 54 thereof instead. As represented in FIG. 7, the luminance components of the original normal image signals are output to the CPU 36 at intervals of one field, and luminance components that are written to the luminance component memory 54 are also output to the CPU 36 at the same intervals of one field, without overlapping with the luminance components of the original normal image signals.

As a result, the CPU 36 calculates the average strength of the luminance signals based on only the luminance components of the normal image signals, so that moving the aperture 38 by the aperture driving circuit 46, to a position where the amount of the white light entering the light guide 34 is extremely increased, is prevented. Thus, the occurrence of halation in a normal image in the plurality images mode is prevented.

In the second embodiment, the difference between the strength of normal image signals that are transmitted to the processor-side image signal processing circuit 48 for generating a pseudo-color image and the strength of fluorescent image signals are remained large, so that deterioration of quality of a pseudo-color image can not be prevented in the pseudo-color image mode, where the normal image signals and the fluorescent image signals are combined.

Figure 8:
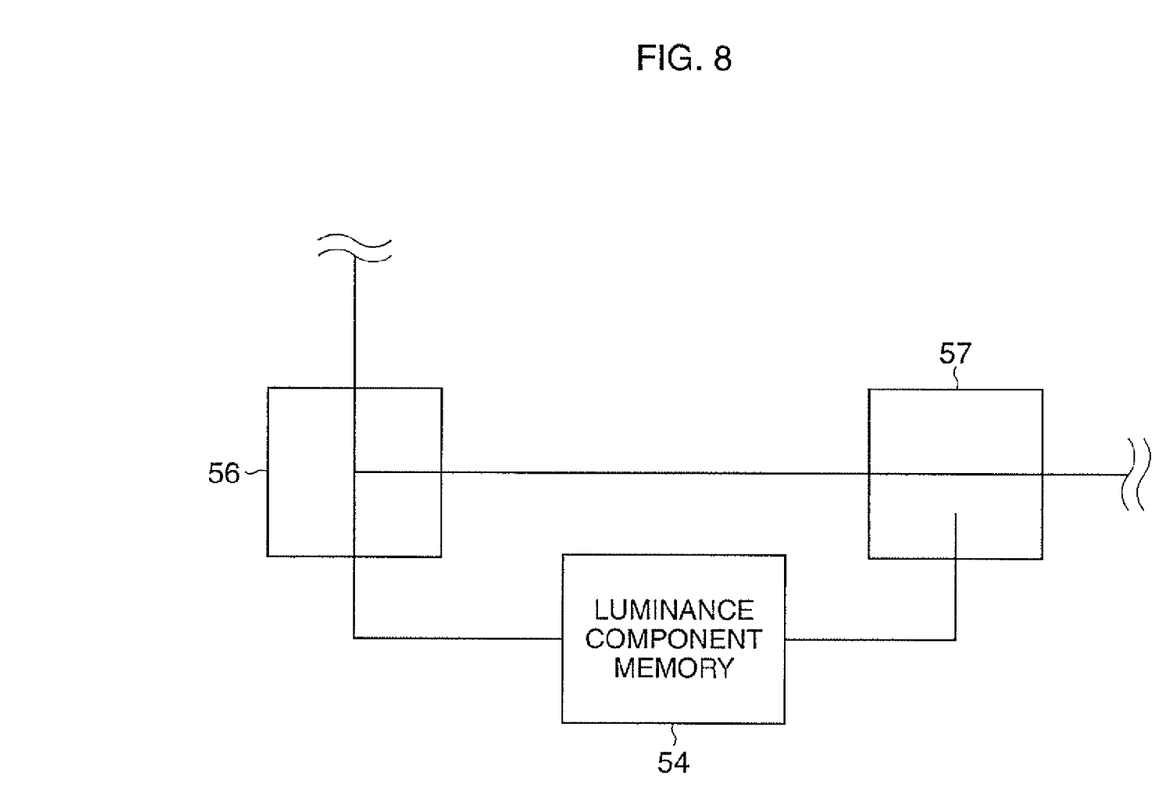
FIG. 8 is a view representing a first transfer switch that is closed and a second transfer switch that is closed on the first transfer switch side.
Figure 9:
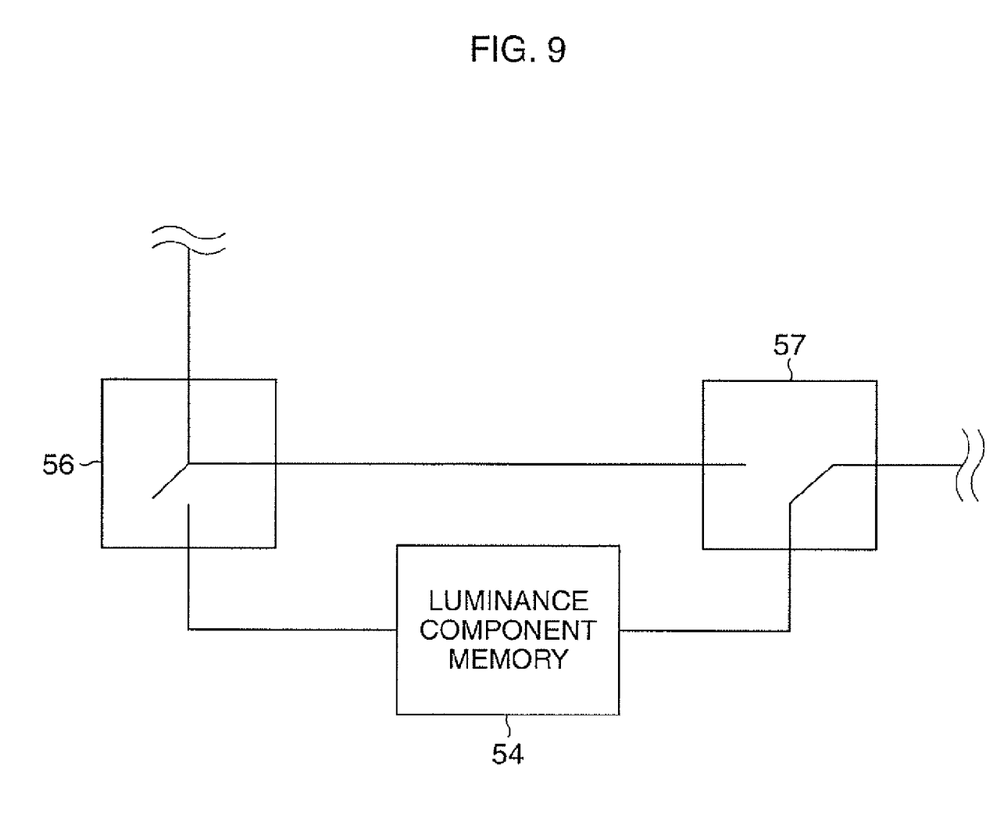
FIG. 9 is a view representing the first transfer switch that is opened and the second transfer switch that is closed on a luminance component memory side.

The state of the first and second transfer switches 56 and 57, represented in FIG. 8, and another state thereof, represented in FIG. 9, are repeated in each one field, under the control of the CPU 36, so that luminance components of only the normal image signals are output to the CPU 36.

That is, the first and second transfer switches 56 and 57 are in the state represented in FIG. 3 during the second field of the first frame represented in FIG. 7, where data representing the luminance component of the normal image signals are transmitted to the CPU 36 via the second transfer switch 57, and are also written to the luminance component memory 54.

Then, the first and second transfer switches 56 and 57 are in the state represented in FIG. 9 during the first field of the second frame represented in FIG. 7, where data representing the luminance component of the normal image signals written to the luminance component memory 54 in the second field of the first frame are transmitted to the CPU 36; on the other hand, data representing the luminance component of the fluorescent image signals are not transmitted to the luminance component memory 54, due to the first transfer switch 56 being opened.

As explained above, in the second embodiment, where the luminance component of only the normal image signals are output to the CPU 36, the same effects as in the first embodiment, where luminance components of the normal image signals are lowered by brightness control of the aperture 38 using the dimmer tables, are obtained. Note that in the second embodiment where the luminance components of the normal image signals are lowered by the amount of white light entering the light guide 34 and are not adjusted by the brightness control of the aperture 38 or other components, the dimmer tables are not required, except for the WL table (see FIG. 6).

The invention is not limited to that described in the preferred embodiment; namely, various improvements and changes may be made to the present invention without departing from the spirit and scope thereof.

The present disclosure relates to subject matter contained in Japanese Patent Application No. 2005-307121 (filed on Oct. 21, 2005) which is expressly incorporated herein, by reference, in its entirety.

The invention claimed is:

1. An electronic endo scope comprising:
a white light source that emits white light for illuminating a subject;
an excitation light source that emits excitation light for generating fluorescent light on the subject;
an imaging device that generates first image signals by receiving reflected light of said white light, said reflected light being reflected on the subject, and that generates second image signals by receiving said fluorescent light;
a light amount controller that controls the amount of said white light, said light amount controller controlling the amount of said white light so that a normal image and a fluorescent image that are both real-time images representing the same subject at the time of receiving said reflected light and said fluorescent light can be generated, said normal image corresponding to said first image signals, and said fluorescent image corresponding to said second image signals;

said light amount controller comprising an aperture and an aperture position controller that controls a position of said aperture;

a data memory, in which aperture control data for controlling said position of said aperture are stored, and a data reader, which reads said aperture control data, wherein said aperture position controller controls said position of said aperture, based on said aperture control data read by said data reader and a luminance signal of said reflected light, said aperture control data comprising data that lowers the amount of said white light and that renders said reflected light luminance and a luminance of said fluorescent light almost identical and said light amount controller lowers the amount of said white light based on said aperture control data, so that a pseudo-color image, comprising a composite of said first image signals and said second image signals, can be generated;

a mode selector that provides a plurality of user selectable modes, said plurality of user selectable modes comprising a normal image mode in which a normal image is generated based on the reflected light of the white light, a fluorescent image mode in which a fluorescent image based on the fluorescent light is generated, a plurality image mode in which a normal image and a fluorescent image are simultaneously generated and a pseudo-color image mode in which a pseudo-color image based on a mixture of the reflected light of the white light and the fluorescent light, is generated; and said data memory comprising a dimmer table for each of at least three of said selectable modes, each dimmer table containing aperture adjustment data and corresponding light amounts to control the amount of white light to be incident onto the subject.

2. The electronic endoscope according to claim 1, wherein said light amount controller controls the amount of said white light to lower the difference between a first luminance component that is the luminance component of said first image signals and a second luminance component that is the luminance component of said second image signals.

3. The electronic endoscope according to claim 1, wherein a plurality of said aperture control data are stored in said data memory, and said data reader reads said aperture control data in accordance with a command of a user.

4. The electronic endo scope according to claim 1, further comprising an image display that displays said normal image and said fluorescent image simultaneously.

5. The electronic endo scope according to claim 1, further comprising a light controller that controls emission of said white light and said excitation light, so that said white light and said excitation light are emitted alternately, each for a predetermined time.

6. The electronic endoscope according to claim 1, said data memory not including a dimmer table for the fluorescent image mode.

7. The electronic endoscope according to claim 1, wherein, when the normal image mode is selected, a first gain value is set, and when the plurality image mode or the pseudo-color image mode is selected a second gain value is set, the second gain value being higher than the first gain value.

8. The electronic endoscope according to claim 1, further comprising a display configured to selectively display each of the generated images in accordance with a selected mode.

9. At electronic endoscope comprising:
a white light source that emits white light for illuminating a subject;
an excitation light source that emits excitation light for generating florescent light on the subject;
an imaging device that generates first image signals by receiving reflected light of said white light, said reflected light being reflected on the subject, and that generates second image signals by receiving said fluorescent light;
a light amount controller that controls the amount of said white light, said light amount controller controlling the amount of said white light so that a normal image and a fluorescent image, that are both real-time images representing the same subject at the time of receiving said reflected light and said fluorescent light can be generated, said normal image corresponding to said first image signals and said fluorescent image corresponding to said second image signals;
said light amount controller comprising an aperture and an aperture position controller that controls a position of said aperture;
a data memory, in which aperture control data for controlling said position of said aperture are stored, and a data reader, which reads said aperture control data, wherein said aperture position controller controls said position of said aperture, based on said aperture control data read by said data reader and a luminance signal of said reflected light, said aperture control data comprising data that lowers the amount of said white light and that renders said reflected light luminance and a luminance of said fluorescent light almost identical and said light amount controller lowers the amount of said white light based on said aperture control data, so that a pseudo-color image, comprising a composite of said first image signals and said second image signals can be generated; and
a mode selector that provides a plurality of user selectable modes, said plurality of user selectable modes comprising a normal image mode in which a normal image is generated based on the reflected light of the white light, a fluorescent image mode in which a fluorescent image based on the fluorescent light is generated, a plurality image mode in which a normal image and a fluorescent image are simultaneously generated and a pseudo-color image mode in which the pseudo-color image based on a mixture of the reflected light of the white light and a fluorescent light is generated; wherein
said data memory stores a plurality of individually selectable aperture adjustment data for each of at least three of said selectable modes.

10. The electronic endoscope according to claim 9, further comprising an image display that displays said normal image and said fluorescent image simultaneously.

11. The electronic endoscope according to claim 9, further comprising a light controller that controls emission of said white light and said excitation light, so that said white light and said excitation light are emitted alternately, each for a predetermined time.

12. The electronic endoscope according to claim 9, said data memory not including a dimmer table for the fluorescent image mode.

13. The electronic endoscope according to claim 9, wherein, when the normal image mode is selected, a first gain value is set, and when the plurality image mode or the pseudo-color image mode is selected a second gain value is set, the second gain value being higher than the first gain value.

* * * * *